(12) United States Patent
Maierhofer

(10) Patent No.: US 11,925,479 B2
(45) Date of Patent: Mar. 12, 2024

(54) METHOD AND APPARATUS FOR DETERMINING THE BODY TEMPERATURE OF A PATIENT

(71) Applicant: FRESENIUS MEDICAL CARE DEUTSCHLAND GMBH, Bad Homburg (DE)

(72) Inventor: Andreas Maierhofer, Schweinfurt (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 1408 days.

(21) Appl. No.: 16/330,229

(22) PCT Filed: Sep. 4, 2017

(86) PCT No.: PCT/EP2017/001053
§ 371 (c)(1),
(2) Date: Mar. 4, 2019

(87) PCT Pub. No.: WO2018/041406
PCT Pub. Date: Mar. 8, 2018

(65) Prior Publication Data
US 2019/0223805 A1 Jul. 25, 2019

(30) Foreign Application Priority Data
Sep. 5, 2016 (DE) .................. 10 2016 010 722.7

(51) Int. Cl.
*A61B 5/145* (2006.01)
*A61B 5/00* (2006.01)
(Continued)

(52) U.S. Cl.
CPC .............. *A61B 5/6866* (2013.01); *A61B 5/01* (2013.01); *A61B 5/746* (2013.01); *A61M 1/1605* (2014.02);
(Continued)

(58) Field of Classification Search
CPC ......... A61B 5/6866; A61B 5/01; A61B 5/746; A61M 1/1605; A61M 1/1607; A61M 1/1609; A61M 1/1664; A61M 1/3609
See application file for complete search history.

(56) References Cited

U.S. PATENT DOCUMENTS 4,083,777 A * 4/1978 Hutchisson ........... A61M 1/153
210/186
6,336,911 B1 1/2002 Westerbeck
(Continued)

FOREIGN PATENT DOCUMENTS

CN         1291875       4/2001
CN       104645433       5/2015
(Continued)

*Primary Examiner* — Guy K Townsend
(74) *Attorney, Agent, or Firm* — Jacobson Holman PLLC

(57) ABSTRACT

The present invention relates to a method of determining the body temperature or a temperature correlated therewith of a patient connected to an extracorporeal blood circuit, wherein the extracorporeal blood circuit has a heat exchanger which is flowed through by blood at one side and by a heat carrier medium at the other side, wherein the temperature ($T_{di}$) of the heat carrier medium at the inlet side is measured at the inlet of the heat exchanger and the temperature ($T_{do}$) of the heat carrier medium at the outlet side is measured at the outlet of the heat exchanger and the volume flow of the heat carrier medium ($Q_d$) is measured; and in that the temperature ($T_{bi}$) of the blood at the inlet side is determined at the inlet of the heat exchanger in accordance with the relationship $T_{bi}=T_{di}$ ($Q_d/D$) ($T_{do}-T_{di}$), where the value D is a value characteristic of the heat transfer by the heat exchanger.

16 Claims, 2 Drawing Sheets

Figure 1:
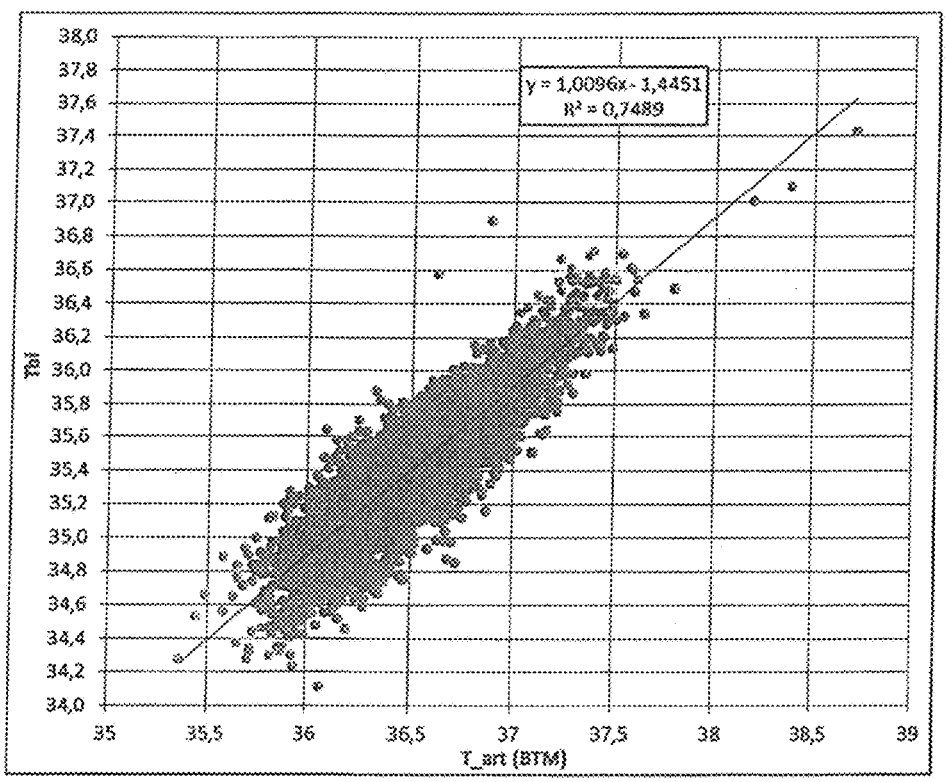

(51) Int. Cl.
  *A61B 5/01* (2006.01)
  *A61M 1/16* (2006.01)
  *A61M 1/36* (2006.01)

(52) U.S. Cl.
  CPC ........ *A61M 1/1607* (2014.02); *A61M 1/1609* (2014.02); *A61M 1/1664* (2014.02); *A61M 1/3609* (2014.02); *A61M 2205/3368* (2013.01); *A61M 2205/366* (2013.01); *A61M 2230/50* (2013.01)

(56) References Cited

U.S. PATENT DOCUMENTS

| | | | | |
|---|---|---|---|---|
| 6,544,727 B1 * | 4/2003 | Hei | ........................ | A61K 35/00 435/173.9 |
| 7,837,042 B2 * | 11/2010 | Yokota | ............... | B01D 67/0095 210/500.36 |
| 8,597,505 B2 * | 12/2013 | Fulkerson | ........... | A61M 1/1696 177/3 |
| 9,033,908 B2 * | 5/2015 | Schilthuizen | ....... | A61M 1/3679 604/6.09 |
| 9,308,307 B2 * | 4/2016 | Fulkerson | ........... | A61M 1/3656 |
| 9,358,331 B2 * | 6/2016 | Fulkerson | ........... | A61M 1/3434 |
| 9,517,296 B2 * | 12/2016 | Fulkerson | .............. | B01D 61/18 |
| 10,258,731 B2 * | 4/2019 | Fulkerson | ........... | A61M 1/166 |
| 10,383,993 B2 * | 8/2019 | Fulkerson | ........... | A61M 1/1694 |
| 10,575,515 B2 * | 3/2020 | Yarmush | ................ | A01N 1/0226 |
| 10,596,310 B2 * | 3/2020 | Fulkerson | ........... | A61M 1/3406 |
| 10,625,014 B2 * | 4/2020 | Pouchoulin | ........... | A61M 1/369 |
| 10,695,481 B2 * | 6/2020 | Kelly | .................. | A61M 1/3482 |
| 10,722,636 B2 * | 7/2020 | Kelly | .................. | A61M 1/3482 |
| 10,857,281 B2 * | 12/2020 | Fulkerson | ........... | A61M 1/166 |
| 11,071,811 B2 * | 7/2021 | Fulkerson | ........... | A61M 1/3413 |
| 11,318,248 B2 * | 5/2022 | Fulkerson | ........... | A61M 1/1694 |
| 2002/0115585 A1 * | 8/2002 | Hei | ....................... | A61L 2/0035 422/68.1 |
| 2002/0192632 A1 * | 12/2002 | Hei | ....................... | A61K 35/16 435/2 |
| 2004/0254419 A1 * | 12/2004 | Wang | ..................... | A61L 31/18 424/1.11 |
| 2005/0025797 A1 * | 2/2005 | Wang | ..................... | B82Y 25/00 424/422 |
| 2005/0079132 A1 * | 4/2005 | Wang | ...................... | A61N 2/06 424/1.11 |
| 2005/0107870 A1 * | 5/2005 | Wang | ..................... | B82Y 25/00 623/1.44 |
| 2007/0010702 A1 * | 1/2007 | Wang | ..................... | A61M 31/10 424/422 |
| 2007/0154570 A1 * | 7/2007 | Miller | .................... | A01N 59/00 424/718 |
| 2008/0044643 A1 * | 2/2008 | Yokota | .................. | B01D 71/68 427/495 |
| 2010/0100027 A1 * | 4/2010 | Schilthuizen | ....... | A61M 1/1696 210/287 |
| 2011/0315611 A1 * | 12/2011 | Fulkerson | ........... | A61M 1/3656 210/96.2 |
| 2012/0226258 A1 * | 9/2012 | Otto | .................... | A61M 1/3679 604/500 |
| 2012/0265117 A1 * | 10/2012 | Fava | .................... | A61M 1/3621 604/6.09 |
| 2013/0220907 A1 * | 8/2013 | Fulkerson | ....... | A61M 1/362227 210/186 |
| 2013/0292319 A1 * | 11/2013 | Fulkerson | ............... | A61M 1/16 210/321.78 |
| 2014/0030231 A1 * | 1/2014 | Yarmush | ............ | G01N 33/5091 435/6.12 |
| 2016/0220748 A1 * | 8/2016 | Pouchoulin | ......... | A61M 1/1601 |
| 2019/0223805 A1 * | 7/2019 | Maierhofer | ............. | A61B 5/01 |

FOREIGN PATENT DOCUMENTS

| | | | |
|---|---|---|---|
| CN | 105664277 | 6/2016 | |
| DE | 60212448 | 12/2006 | |
| DE | 60225472 | 4/2009 | |
| EP | 0265795 | 5/1988 | |
| EP | 265795 A * | 5/1988 | .......... A61M 1/1656 |
| EP | 0773035 | 5/1997 | |
| EP | 773035 A2 * | 5/1997 | ............. A61M 1/16 |
| WO | WO 03/055544 | 7/2003 | |
| WO | WO-03055544 A1 * | 7/2003 | ........... A61M 1/367 |
| WO | WO 2016/025268 | 2/2016 | |
| WO | WO-2016025268 A2 * | 2/2016 | .......... A61F 7/0085 |

* cited by examiner

METHOD AND APPARATUS FOR DETERMINING THE BODY TEMPERATURE OF A PATIENT

The present invention relates to a method and to an apparatus for determining the body temperature or a temperature correlated therewith of a patient connected to an extracorporeal blood circuit, wherein the extracorporeal blood circuit has a heat exchanger which is flowed through by blood at one side and by a heat transfer medium at the other side.

It is known from the prior art to measure the body temperature of a dialysis patient before and during the dialysis treatment. This is an important indicator for the physiological state of the patient, for example during hemodialysis treatment or a hemodiafiltration treatment.

The body temperature of the patient before the treatment is substantially determined by his biorhythm and may be elevated by illness such as inflammation.

The dialysis treatment itself can likewise influence the body temperature by different factors. An excitation of the catabolism during the treatment and equally the reduction of the blood volume by ultrafiltration produce a slight increase in body temperature, for example. Greater and faster increases in temperature can be caused, for example, by intolerance reactions to the dialysis treatment which are caused by the contact of blood with components of the dialyzer or of the remaining extracorporeal system or by intradialytic medication administration.

A greater displacement of the blood circulation into the periphery of the body takes place by physiological regulatory mechanisms as a counter-reaction of the body on an exceeding of specific temperature thresholds to cool the body down. This displacement, however, simultaneously results in a lowering of the central blood pressure, which can result, together with the volume withdrawal due to the ultrafiltration taking place during the treatment, in a drop in blood pressure.

Against this background, the measurement of the body temperature before and during the dialysis treatment is of diagnostic value. Apart from this, critical states during the dialysis can be recognized by the measurement of the body temperature and counter-measures can be taken. The control of the dialysis temperature with the body temperature as an input value is, for example, conceivable to be able to carry out a safe and comfortable dialysis treatment.

A disadvantage of the measurement of the body temperature is the additional apparatus and personnel effort associated therewith.

In clinical practice, the measurement of the body temperature takes place using a medical thermometer, either by contact or as an infrared measurement. The evaluation of the measured value takes place by the carers who draw conclusions on the state of the patient from the measured value and adapt the dialysis temperature as required. Such measurements generally only take place when the patient shows specific symptoms so that intradialytic changes of the body temperature are not noticed or are only noticed rarely.

Automated continuous measurements are also known from the prior art in which a measurement is taken at the arterial blood hose of the extracorporeal blood circuit and in which a conclusion on the body temperature is drawn from the measurement of the temperature drop between the puncture position and the measurement site. The sensors used for this purpose are available as additional parts, which is accompanied by additional procurement costs and an additional effort on the insertion of the hose system into the sensor heads.

It is therefore the underlying object of the present invention to provide a method and an apparatus by means of which it is possible to detect or approximate the absolute value and/or the development of the body temperature of the patient without any additional hardware solely using the elements already present in the hydraulics, i.e. e.g. solely using the elements already present in the dialyzate system of a dialysis machine, in particular by means of the sensors anyway present there.

It is pointed out at this point that the method in accordance with the invention and the apparatus in accordance with the invention are not restricted to dialysis, but rather also cover other treatment methods for patients in which extracorporeal blood circuits are used such as in therapeutic hypothermia, in which the blood is cooled to a specific temperature value below the physiological value.

This named object is achieved by a method having the means of claim 1 as well as by an apparatus having the features of claim 9.

Provision is accordingly made that the temperature ($T_{di}$) of the heat carrier medium such as the dialyzate or a temperature fluid for setting the temperature of the blood at the inlet side is measured at the inlet of the heat exchanger (also called a "heat exchanging device" in the following) and the temperature ($T_{do}$) of the heat carrier medium at the outlet side is measured at the outlet of the heat exchanger and the volume flow of the heat carrier medium ($Q_d$) is measured and such that the temperature ($T_{bi}$) of the blood at the inlet side is determined at the inlet of the heat exchanger in accordance with the relationship $$T_{bi}=T_{di}+(Q_d/D)(T_{do}-T_{di}) \quad (1)$$

where the value D is a value characteristic of the heat transfer by the heat exchanger. It can be seen from formula (1) that no measurement has to be carried out at the blood side to determine the temperature value for the blood. Measurements of the temperature of the dialyzate or of another heat carrier medium before and after the dialyzer/heat exchanger as well as the measurement of the volume flow of the dialyzate or of the heat carrier medium are sufficient.

In accordance with Fourier's Law, the heat flow J between two compartments is proportional to their temperature difference. In the case of a dialyzer, these compartments are formed by the space flowed through by blood, on the one hand, and by the space flowed through by dialyzate, on the other hand. The space flowed through by blood typically comprises the inner spaces of a hollow fiber bundle and the space flowed through by dialyzate comprises the space surrounding it.

It is pointed out at this point that the expression that the heat exchanger is flowed through by blood at one side and by a heat carrier medium at the other side covers the case that respectively exactly one compartment or space is provided for the blood and one for the heat carrier medium and also the case that a plurality of compartments or spaces are present for the blood and/or for the heat carrier medium.

It is pointed out in another respect that the term "a" or "one" used within the framework of the invention covers both the case that exactly one of the elements is present and the case that a plurality of the elements in question are present.

If a dialyzer is assumed as the heat exchanger or heat exchanging device, J=D ($T_{bi}-T_{di}$) results for the heat flow J, where $T_{bi}$ is the inlet temperature into the dialyzer at the blood side and $T_{di}$ is the inlet temperature into the dialyzer at the dialyzate side.

D is a value which describes the heat exchange or transfer in the dialyzer or heat exchanger. D depends on the geometrical design and on the material properties of the dialyzer or heat exchanger, on the substance properties of the blood and of the dialyzate or of the heat carrier medium and on the flow rates of the blood and of the dialyzate or of the heat carrier medium.

The references made above and in the following with respect to the dialyzer and the dialyzate are representative for any desired heat exchanger and any desired heat carrier medium.

The heat flow input into the dialyzate also has to be transported away again by means of the dialyzate while neglecting radiation losses (energy maintenance) so that $J=Q_d (T_{do}-T_{di})$ also applies to J, where $T_{do}$ is the outlet temperature from the dialyzer at the dialyzate side and $Q_d$ is the dialyzate flow, i.e. the volume flow of the dialyzate through the dialyzer.

If the two formulas are combined, the above relationship (1) results:

$$T_{bi}=T_{di}+(Q_d/D)(T_{do}-T_{di}) \quad (1)$$

The blood temperature at the inlet of the dialyzer can thus be determined with a known D solely by means of values which are measured at the dialyzate side or are known there. The lack of a sign or of an indicated operator between the bracket expressions $(Q_d/D)$ and $(T_{do}-T_{di})$ is to be understood as a multiplication of the bracket expressions. This applies accordingly to all the formulas named within the framework of the invention.

The value D can be determined in that the methods are applied such as are used for determining the dialysance for the diffuse mass transfer in a dialyzer. We refer in this connection to the standard work: Replacement of Renal Function by Dialysis", 4th edition; Chapter 2, "Principles and Biophysics of Dialysis" (Sargent & Gotch), pp. 69-74 and Chapter 9, "Hemodialysis Fluid Composition" (C. Ronco et al) pp. 263-266.

The body temperature and also a value correlated therewith such as the blood temperature in the extracorporeal blood circuit can be determined by the method in accordance with the invention and by the apparatus in accordance with the invention.

In a conceivable embodiment of the invention, the value D is determined, with a known characteristic $k_0$ A of the heat exchanger, from the relationship $$D=Q_b(e^\gamma-1)/(e^\gamma-(Q_b/Q_d)) \quad (2)$$

where $\gamma=k_0 A (Q_d-Q_b)/(Q_d Q_b)$ or $$D=Q_b(1-e^\gamma)/(1+(Q_b/Q_d)) \quad (3)$$

where $\gamma=k_0 A (Q_d+Q_b)/(Q_d Q_b)$
with the formula (2) applying to the flowing through of the heat exchanger by blood and heat carrier medium in a counter flow and the formula (3) applying to the flowing through of the heat exchanger by blood and heat carrier medium in coflow, and with the value $Q_b$ representing the volume flow of the blood through the heat exchanger.

If the value $K_0$ A of the heat exchanger is not known, D (or also $K_0$ A using equations (2) and (3)) can be determined analogously to the determination of the diffuse dialyzer clearance by temperature variations at the dialyzate side, e.g. in the form of pulse profiles or stage profiles.

This requires the time development $T_j$ for a temperature variation pulse j of the temperature of the dialyzate to be measured at the dialyzer inlet and dialyzer outlet and for the area below the temperature curve to be determined by integral formation.

Using the pulse method, $$D=Q_d(1-A_{do}/A_{di}) \quad (4)$$

then results for D, where $A_{do}$ represents the area, optionally corrected by a baseline, below the temperature curve over time at the outlet side of the heat exchanger and $A_{di}$ represents the area, optionally corrected by a baseline, below the temperature curve over time at the inlet side of the heat exchanger.

The areas $A_{do}$ or $A_{di}$, generally $A_j$, are thus $A_j=\int T_j(t)dt - BL_j$, for the respective pulse, where $BL_0$ represents a suitably determined baseline for the pulse j.

It is furthermore conceivable that the value D is determined from the relationship $$D=fQ_b \quad (5)$$

where provision is preferably made that the value f is 1 or is in the range 1±0.1 or 1±0.2. This recognition is based on the fact that, in contrast to the mass transfer, the heat exchange or heat transition is largely independent of properties of the pores determining the substance diffusion and also takes place without direct contact of the two liquids to one another. D can thus also be assumed as proportional to the blood flow $Q_b$ in simplified terms.

The value 1 can be used for f in a first approximation.

It is also possible to determine the value $T_{bi}$ in accordance with formula (1) and to compare it with measured values of the blood temperature. f can thus be determined as a fit factor for different types of dialyzers or heat exchangers and can be placed in table form in a calculation unit of the dialysis machine or of the treatment device.

It is furthermore conceivable that the blood temperature in the extracorporeal blood circuit is measured for the purpose of the later estimation of the blood temperature or body temperature and a relationship between the measured value ($T_{art}$) (blood temperature in the arterial line of the extracorporeal blood circuit) and the value $T_{bi}$ determined in accordance with formula (1) is established by regression, preferably by a linear regression. A regression equation of the type $$T_{art}=a\,T_{bi}+b \quad (6)$$

can thus be prepared, for example, where the coefficients a and b can e.g. be determined by a least square method.

This relationship can then be used to determine the value for $T_{art}$ from the values $T_{bi}$ determined in accordance with formula (1). This value can then be used, for example, to determine the body temperature $T_{Körper}$.

This can take place, for example according to the relationship $$T_{Körper}=T_{Umgebung}+(T_{art}-T_{Umgebung})\exp(\alpha L/Q_b) \quad (7)$$

where $\alpha$ is the thermal conductivity per length unit of the hose piece of the extracorporeal circuit between the arterial vessel port and the heat exchanger, $T_{Umgebung}$ is the environmental temperature and L is the length of this hose piece.

It results from equation (7) that the body temperature substantially corresponds to the temperature $T_{art}$ at high values for $Q_b$.

Provision is made in a conceivable embodiment of the invention that the determined body temperature or the value correlated therewith is used to set the dialysis temperature based thereon. If the e.g. determined value of the body temperature is too low, the dialysis temperature is raised and vice versa. A feedback loop is also conceivable in which the determined body temperature or the value correlated therewith represents the regulation value and is maintained at a desired value or in a desired value range by means of the dialyzate temperature as a control variable. The applies to the method in accordance with the invention and also to the apparatus in accordance with the invention.

It is furthermore conceivable that the dialyzate temperature can be used as an input value for any desired regulations and profiles.

Provision can furthermore be made that the output of an alarm takes place if the body temperature or a value correlated therewith exceeds or falls below a limit value or a limit value range. The same applies accordingly not only to the absolute value of the body temperature or of the value correlated therewith, but also to the change of the body temperature or of the value correlated therewith with respect to another value, in particular with respect to the outlet temperature, i.e. a delta monitoring is also covered by the invention. This finally also applies accordingly to the detection of the speed of the change of the body temperature or of the value correlated therewith. If it exceeds or falls below a limit value or limit value range, an alarm can likewise be output.

Any desired information which can be perceived by the user or the medical staff is to be understood by the term "alarm" such as an alarm sound in the narrower sense or a communication in text form.

The present invention furthermore relates to an apparatus for determining the body temperature or a temperature correlated therewith of a patient having an extracorporeal blood circuit, wherein the extracorporeal blood circuit has a heat exchanger which is flowed through by blood at one side and by a heat carrier medium at the other side; wherein the apparatus has measurement sensors which are arranged to measure the temperature ($T_{di}$) of the heat carrier medium at the inlet side at the inlet of the heat exchanger and to measure the temperature ($T_{do}$) of the heat carrier medium at the outlet side at the outlet of the heat exchanger and to measure the volume flow of the heat carrier medium ($Q_d$); and wherein the apparatus has a calculation unit which is configured to determine the temperature ($T_{bi}$) of the blood at the at the inlet side at the inlet of the heat exchanger in accordance with the relationship $$T_{bi}=T_{di}+(Q_d/D)(T_{do}-T_{di}) \quad (1)$$

where the value D is a value characteristic of the heat transfer by the heat exchanger.

It is conceivable that the heat exchanger is a dialyzer and/or that the temperature correlated with the body temperature is the temperature of the blood in the extracorporeal circuit.

Provision can furthermore be made that the apparatus has calculation means which are configured to determine the value D, with a known characteristic $k_0$ A of the heat exchanger, from the relationship $$D=Q_b(e^\gamma-1)/(e^\gamma-(Q_b/Q_d)) \quad (2)$$

where $\gamma=k_0$ A $(Q_d-Q_b)/(Q_dQ_b)$ or $$D=Q_b(1-e^\gamma)/(1+(Q_b/Q_d)) \quad (3)$$

where $\gamma=k_0$ A $(Q_d+Q_b)/(Q_dQ_b)$ with the formula (2) applying to the flowing through of the heat exchanger in a counter flow and the formula (3) applying to the flowing through of the heat exchanger in coflow, and with the value $Q_b$ representing the volume flow of the blood through the heat exchanger.

The apparatus can have calculation means for determining the value D, said calculation means being configured to generate a temperature variation at the side of the heat carrier medium and to integrate the time development of the temperature of the heat carrier medium at the inlet and at the outlet or at the measurement points over time and to determine the value D from the relationship $$D=Q_d(1-A_{do}/A_{di}) \quad (4)$$

where $A_{do}$ represents the area, optionally corrected by a baseline, below the temperature curve over time at the outlet side of the heat exchanger and $A_{di}$ represents the area, optionally corrected by a baseline, below the temperature curve over time at the inlet side of the heat exchanger.

The apparatus can furthermore have calculation means which are configured to determine the value D from the relationship $$D=fQ_b \quad (5)$$

where provision is preferably made that the value f is 1 or is in the range 1±0.1 or 1±0.2.

Provision is made in a further embodiment of the invention that a measuring sensor is provided to measure the blood temperature in the extracorporeal circuit for the purpose of determining a correlation between calculated values and actual values and that regression means are provided which are configured to prepare a regression equation between the measured value ($T_{art}$) and the value determined in accordance with formula (1) by regression, preferably by linear regression.

This can read $$T_{art}=a\ T_{bi}+b \quad (6)$$

for example.

It is furthermore conceivable that the apparatus has calculation means which are configured to calculate $T_{art}$ from the regression equation and to determine the body temperature in accordance with the equation $$T_{Körper}=T_{Umgebung}+(T_{art}-T_{Umgebung})\exp(\alpha L/Q_b) \quad (7)$$

where α is the thermal conductivity per length unit of the hose piece of the extracorporeal circuit between the arterial vessel port and the heat exchanger and L is the length of this hose piece.

As stated above, setting means can be present by means of which the dialyzate temperature can be varied.

This or a regulator can have the determined body temperature or the value correlated therewith as an inlet value and can set the dialyzate temperature, which serves as a control variable, in dependence thereon. A regulator can be provided in this respect to which the determined body temperature or the value correlated therewith is supplied as actual values and which calibrates them to a desired value or in a desired value range by means of the dialyzate temperature.

The apparatus can furthermore have at least one alarm device which is suitable to output an alarm when the body temperature or a value correlated therewith exceeds or falls below a limit value or a limit value range. The same applies accordingly not only to the absolute value of the body temperature or of the value correlated therewith, but also to the change of the body temperature or of the value correlated therewith with respect to another value, in particular with respect to the outlet temperature, i.e. a delta monitoring is also covered by the invention. This finally also applies accordingly to the detection of the speed of the change of the body temperature or of the value correlated therewith. If it exceeds or falls below a limit value or limit value range, an alarm can likewise be output by means of the alarm apparatus.

Any desired information which can be perceived by the user or the medical staff is to be understood by the term "alarm" such as an alarm sound in the narrower sense or a communication in text form.

Alternatively or additionally, the apparatus can comprise monitoring means for monitoring one or more of the named values (absolute value of the body temperature or of the value correlated therewith; its difference with respect to a reference value; its change speed).

The present invention furthermore relates to a blood treatment device, in particular to a dialysis machine, which is characterized in that the blood treatment device is designed with an apparatus in accordance with one of the claims 8 to 14 and/or has means for carrying out a method in accordance with one of the claims 1 to 7.

Further details and advantages of the invention will be explained in more detail with reference to an embodiment shown in the drawing.

Figure 2:
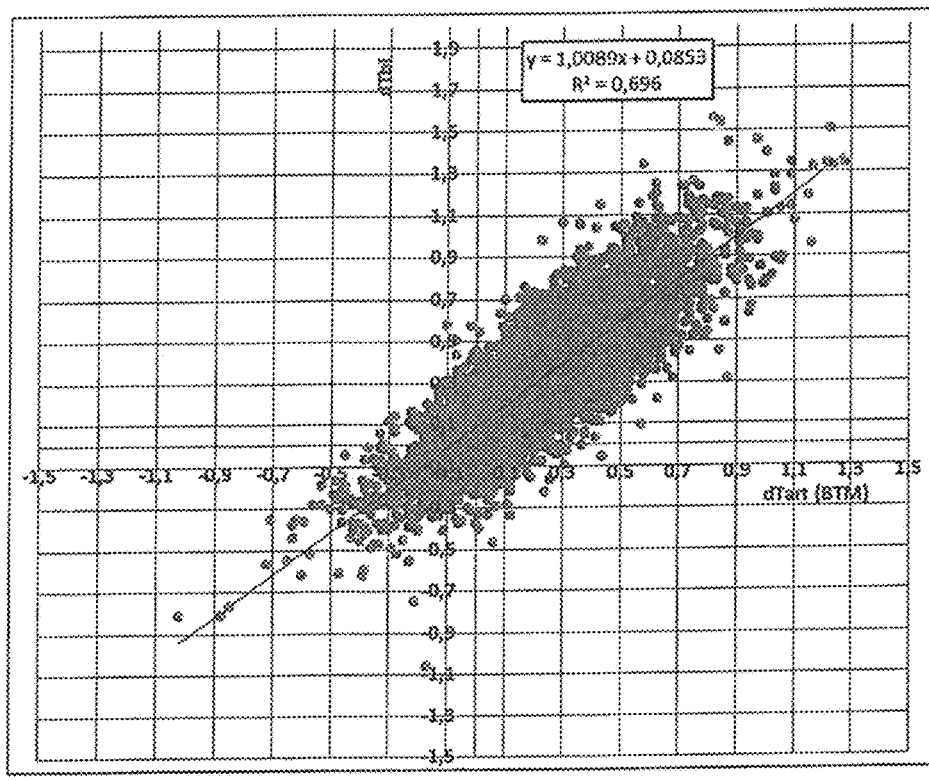
Figure 3:
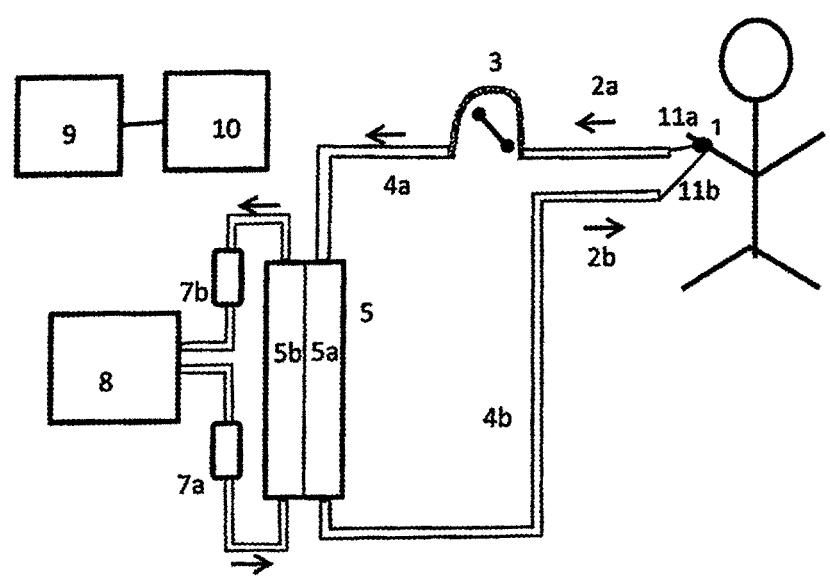

There are shown:

FIG. 1: a comparison of the values of the blood temperature (Tbi) calculated in accordance with formulas (1) and (5) and the measured values of the temperature (T_art (BTM)) of the blood in the arterial part of the extracorporeal circuit at the start of dialysis in ° C.;

FIG. 2: a comparison of the calculated (dTbi) temperature change and of the measured change of the arterial blood temperature (dTart (BTM) during the dialysis; and FIG. 3: a schematic representation of a dialysis machine in accordance with the invention.

FIG. 1 shows a comparison of calculated values and measured values for the arterial blood temperature of a patient at a start of dialysis on the data basis of 5000 values or treatments. The blood flow $Q_b$ amounted to 350-450 ml/min and the dialyzate flow $Q_d$ amounted to 500-700 ml/min. The value for D was calculated in accordance with formula (5) with f=1.1.

FIG. 1 illustrates a good correlation between the calculation in accordance with the invention at the dialyzate side and the measurement of the temperature at the blood side, with the standard deviation of the difference of the two methods lying at 0.19° C. The systematic deviation can be determined by a correction with the aid of the coefficients determined from the regression in accordance with the formula $T_{art} = a\ T_{bi} + b$.

In addition to an automatic registration and documentation of the body temperature at the start of the treatment, an automated monitoring for an exceeding of a threshold value can alternatively or additionally also take place with corresponding information to the nurse or physician. This can be necessary in order e.g. to draw attention to an inflammation.

It is additionally or alternatively also conceivable that an alarm is output when the body temperature or its difference from a reference value such as from the starting value of the body temperature at the start of treatment or when its change speed exceeds or falls below a limit value or a limit value range.

In the example shown in FIG. 1, the exceeding of an arterially measured temperature of 37.2° can be recognized with a sensitivity of 82% and a specificity of 98% by the measurement at the dialyzate side.

FIG. 2 shows a comparison of values calculated in accordance with the invention, i.e. by sensors at the dialyzate side, and measured values for the change of the arterial blood temperature of a patient during the treatment on the data basis of 5000 values or treatments. The blood flow $Q_b$ amounted to 350-450 ml/min and the dialyzate flow $Q_d$ amounted to 500-700 ml/min. The value for D was calculated in accordance with formula (5) with f=1.1. A good correlation between the calculation in accordance with the invention at the dialyzate side and the measurement at the blood side is also shown here, with the standard deviation of the difference of the methods amounting to 0.17° C.

In accordance with the invention, a monitoring of the intradialytic change of the patient temperature is thus also possible.

As initially stated, a temperature increase can be an indication of an intolerance reaction, or a drop in blood pressure can result due to a temperature increase brought about by any causes.

Due to the detection of the temperature change which preferably runs automatically, the dialysis machine can automatically output a warning against possible intolerance reactions, i.e. have corresponding output means, warn against possible impending drops in blood pressure, trigger a blood pressure measurement in an automated manner or increase its frequency, or lower the dialyzate temperature to counteract the increase in the body temperature or also to carry out a plurality of the aforesaid measures. The dialysis machine or other treatment device can have means to carry out one or more of these measures.

In the example shown in FIG. 2, the presence of a temperature increase of more than 0.5° can be recognized with a sensitivity of 73% and a specificity of 90% by the measurement at the dialyzate side.

As already stated above, the temperature determined in accordance with formula (1) or the temperature determined in accordance with $T_{art} = a\ T_{bi} + b$ or the temperature determined in accordance with formula (7) can be used as an input value for the regulation of this temperature to a desired value or in a desired value range, for which purpose the temperature control unit 8 shown in FIG. 3 can be used and for which purpose the device has a regulation unit 9.

The keeping constant of the temperature at the start of the dialysis is in particular possible using the method in accordance with the invention or using the apparatus in accordance with the invention without substantial losses in precision with respect to the method based on the measurement with sensors at the blood side since systematic deviations between the procedure in accordance with the invention and the reference are of no significance here.

In accordance with the invention, only elements which are anyway present at a dialysis machine are preferably used for the temperature measurement, which brings along cost advantages. Temperature sensors arranged at the blood side can thus be dispensed with, for example.

FIG. 3 shows a dialysis machine by means of which the method in accordance with the invention can be carried out or a dialysis machine in accordance with the invention. The blood pump 3 conveys blood out of the vessel port 1 via a first arterial needle 11a in the direction 2a and via a first blood line 4a to the blood side 5a of a dialyzer or other heat exchanger or heat exchanging device (both terms are used synonymously within the framework of the invention).

The blood side 5a is in thermal contact with the dialyzate side 5b or with a second compartment 5b of the dialyzer 5 via one or more membranes.

If it is a hemodialysis or hemodiafiltration, 5b is the dialyzate side of a dialyzer; with an apparatus for blood temperature control, it is the side of the heat exchanging device flowed through by a heat medium or a coolant.

For the temperature control of the dialyzate or of the heat medium/coolant, the temperature control unit 8 serves as an adjustment member which can have elements such as heating and/or cooling elements, temperature sensors and regulation apparatus controlled in an analog or digital manner.

The temperature of the liquid flowing into the second compartment 5b is measured upstream and downstream of the second compartment 5b by means of the temperature sensors 7a, 7b. The temperature control unit 8 can be controlled by the evaluation and/or regulation unit 9 with the aim of changing the blood temperature in the second blood line 4b by means of which the blood is conveyed through the venous port 11b in the direction 2b back to the patient.

Apart from the sensors 7a, 7b, means for determining the liquid flow at the blood side and at the secondary side, i.e. at the dialyzate side, are also connected to the regulation unit 9.

To determine the blood temperature in the line sections 4a and 4b and the body temperature and/or its time variations in the course of treatment, different calculations, described in more detail above, are carried out in the evaluation unit 9 and the results can be communicated to a display unit 10 or also via a different kind of communication such as over a network or a wireless communication such as to a smartphone.

The invention claimed is:

1. A method of determining the body temperature or of a temperature correlated therewith of a patient connected to an extracorporeal blood circuit, wherein the extracorporeal blood circuit has a heat exchanger which is flowed through by blood at one side and by a heat carrier medium at the other side, characterized in that the temperature (LH) of the heat carrier medium at the inlet side is measured at the inlet of the heat exchanger and the temperature (Tao) of the heat carrier medium at the outlet side is measured at the outlet of the heat exchanger and the volume flow of the heat carrier medium ($Q_d$) is measured; and in that the temperature ($T_{bi}$) of the blood at the inlet side is determined at the inlet of the heat exchanger in accordance with the relationship $$T_{bi}=T_{di}+(Q_d/D)(T_{do}-T_{di}) \quad (1)$$

where the value D is a value characteristic of the heat transfer by the heat exchanger.

2. A method in accordance with claim 1, characterized in that the heat exchanger is a dialyzer; and/or in that the temperature correlated with the body temperature is the temperature of the blood in the extracorporeal circuit; and/or in that the calculated temperature is supplied as an actual value to a regulation and the temperature regulation of the body temperature or of the temperature correlated therewith is carried out using the change of the temperature of the heat carrier medium as the adjustment value.

3. A method in accordance with claim 1, characterized in that the value D is determined, with a known characteristic $k_0$ A of the heat exchanger, from the relationship $$D=Q_b(e^{\gamma}-1)/(e^{\gamma}-(Q_b/Q_d)) \quad (2)$$

where $\gamma=k_0$ A $(Q_d-Q_b)/(Q_dQ_b)$ or $$D=Q_b(1-e^{\gamma})/(1+(Q_b/Q_d)) \quad (3)$$

with the formula (2) applying to the flowing through of the heat exchanger in a counter flow and the formula (3) applying to the flowing through of the heat exchanger in coflow, and with the value $Q_b$ representing the volume flow of the blood through the heat exchanger.

4. A method in accordance with claim 1, characterized in that the value D is measured in that a temperature change is carried out at the side of the heat carrier medium and the time development of the temperature of the heat carrier medium at the inlet and at the outlet is integrated over time and the value D is determined from the relationship $$D=Q_d(1-A_{do}/A_{di}) \quad (4)$$

where $A_{do}$ represents the area, optionally corrected by a baseline, below the temperature curve over time at the outlet side of the heat exchanger and $A_{di}$ represents the area, optionally corrected by a baseline, below the temperature curve over time at the inlet side of the heat exchanger.

5. A method in accordance with claim 1, characterized in that the value D is determined from the relationship $$D=fQ_b \quad (5)$$

where provision is preferably made that the value f is 1 or is in the range 1±0.1 or 1±0.2.

6. A method in accordance with claim 1, characterized in that the blood temperature in the extracorporeal circuit is measured and a relationship is established between the measured value ($T_{art}$) and the value determined in accordance with formula (1) by regression, preferably by linear regression, preferably in accordance with the relationship $$T_{art}=a \, T_{bi}+b \quad (6)$$

with provision preferably being made that $T_{art}$ is calculated from the regression equation and that the body temperature is determined in accordance with the relationship $$T_{Körper}=T_{Umgebung}+(T_{art}-T_{Umgebung})\exp(\alpha L/Q_b) \quad (7)$$

where $\alpha$ is the thermal conductivity per length unit of the hose piece of the extracorporeal circuit between the arterial vessel port and the heat exchanger and L is the length of this hose piece.

7. A method in accordance with claim 1, characterized in that the body temperature or a value correlated therewith, its difference with respect to a reference value and/or its change speed is monitored, with provision preferably being made that an alarm is output on an exceeding or falling below of a limit value or limit value range of one of the aforesaid values.

8. An apparatus for determining the body temperature or a temperature correlated therewith of a patient having an extracorporeal blood circuit, wherein the extracorporeal blood circuit has a heat exchanger which is flowed through by blood at one side and by a heat carrier medium at the other side; characterized in that the apparatus has measurement sensors which are arranged to measure the temperature ($T_{di}$) of the heat carrier medium at the inlet side at the inlet of the heat exchanger and to measure the temperature ($T_{do}$) of the heat carrier medium at the outlet side at the outlet of the heat exchanger and to measure the volume flow of the heat carrier medium ($Q_d$); and in that the apparatus has a calculation unit which is configured to determine the temperature ($T_{bi}$) of the blood at the inlet side at the inlet of the heat exchanger in accordance with the relationship $$T_{bi}=T_{di}+(Q_d/D)(T_{do}-T_{di}) \quad (1)$$

where the value D is a value characteristic of the heat transfer by the heat exchanger.

9. An apparatus in accordance with claim 8, characterized in that the heat exchanger is a dialyzer and/or that the temperature correlated with the body temperature is the temperature of the blood in the extracorporeal circuit.

10. An apparatus in accordance with claim 8, characterized in that the apparatus comprises calculation means which are configured to determine the value D, with a known characteristic $k_0$ A of the heat exchanger, from the relationship $$D=Q_b(e^\gamma-1)/(e^\gamma-(Q_b/Q_d)) \quad (2)$$

where $\gamma=k_0 \, A \, (Q_d-Q_b)/(Q_d Q_b)$ or $$D=Q_b(1-e^\gamma)/(1+(Q_b/Q_d)) \quad (3)$$

with the formula (2) applying to the flowing through of the heat exchanger in a counter flow and the formula (3) applying to the flowing through of the heat exchanger in coflow, and with the value $Q_b$ representing the volume flow of the blood through the heat exchanger.

11. An apparatus in accordance with claim 8, characterized in that the apparatus comprises calculation means for determining the value D which are configured to carry out a temperature change at the side of the heat carrier medium and to integrate the time development of the temperature of the heat carrier medium at the inlet and at the outlet over time and to determine the value D from the relationship $$D=Q_d(1-A_{do}/A_{di}) \quad (4)$$

where $A_{do}$ represents the area, optionally corrected by a baseline, below the temperature curve over time at the outlet side of the heat exchanger and Ad; represents the area, optionally corrected by a baseline, below the temperature curve over time at the inlet side of the heat exchanger; and/or in that the apparatus comprises calculation means which are configured to determine the value D from the relationship $$D=fQ_b \quad (5)$$

where provision is preferably made that the value f is 1 or is in the range 1±0.1 or 1±0.2.

12. An apparatus in accordance with claim 8, characterized in that the apparatus has monitoring means and/or alarm means which are designed to monitor the body temperature or a value correlated therewith or its difference with respect to a reference value and/or its change speed, with provision preferably being made that an alarm is output on an exceeding or falling below of a limit value or limit value range of one of the aforesaid values.

13. An apparatus in accordance with claim 8, characterized in that the apparatus is configured to determine the body temperature from a calculated or known value for $T_{art}$ in accordance with the relationship $$T_{Körper}=T_{Umgebung}+(T_{art}-T_{Umgebung})\exp(\alpha L/Q_b) \quad (7)$$

where $\alpha$ is the thermal conductivity per length unit of the hose piece of the extracorporeal circuit between the arterial vessel port and the heat exchanger and L is the length of this hose piece.

14. An apparatus in accordance with claim 8, characterized in that the apparatus has a regulation unit which is configured to regulate the body temperature of the patient or a temperature correlated therewith to a desired value or into a desired value range, wherein the regulation unit has an input for the calculated temperature as an actual value and is configured to compare it to a desired value or desired value range, and wherein the regulation unit is connected to an adjustment unit, in particular to a temperature control unit, which is configured to change the temperature of the dialyzate serving as an adjustment value if the actual value does not correspond to the desired value or if it does not lie in the desired value range.

15. A blood treatment device, in particular a dialysis machine, characterized in that the blood treatment device is formed with an apparatus in accordance with claim 8.

16. A blood treatment device, in particular a dialysis machine, characterized in that the blood treatment device has means for carrying out a method in accordance with claim 1.

* * * * *